United States Patent [19]

Rzeszotarski et al.

[11] Patent Number: 4,657,899

[45] Date of Patent: Apr. 14, 1987

[54] ANTAGONISTS OF SPECIFIC EXCITATORY AMINO ACID NEUROTRANSMITTER RECEPTORS

[75] Inventors: Waclaw J. Rzeszotarski, Millersville; Robert L. Hudkins; Maria E. Guzewska, both of Baltimore, all of Md.

[73] Assignee: Nova Pharmaceutical Corporation, Baltimore, Md.

[21] Appl. No.: 849,696

[22] Filed: Apr. 9, 1986

[51] Int. Cl.[4] .......................... C07F 9/38; A61K 31/04; A61K 31/135; A61K 31/195
[52] U.S. Cl. .............. 514/120; 260/502.5 D; 514/113; 514/114; 558/190; 558/192; 558/193
[58] Field of Search ............... 260/502.5 D; 514/120, 514/113, 114; 558/198, 190, 192, 193

[56] References Cited

U.S. PATENT DOCUMENTS

| 2,915,547 | 12/1959 | Atherton | 558/190 |
| 2,966,074 | 7/1960 | Atherton | 558/190 |
| 3,754,085 | 8/1973 | Christensen et al. | 260/502.5 D |
| 4,061,697 | 12/1977 | Hubner et al. | 558/190 |

FOREIGN PATENT DOCUMENTS 431171 2/1975 U.S.S.R. .............. 260/502.5 D

OTHER PUBLICATIONS

Obrycki et al, J. Org. Chem, vol. 33, No. 2, Feb. 1968, pp. 632–636.
Doak et al, Antibiotics and Chemotherapy, vol. 8 (1958) pp. 342–348.

Primary Examiner—J. E. Evans
Attorney, Agent, or Firm—Breneman, Georges, Hellwege & Yee

[57] ABSTRACT

The invention pertains to novel, potent anticonvulsants, analgesics and cognition enhancers achieving their action through the antagonism of specific excitatory amino acid neurotransmitter receptors. In particular, the invention is directed to ω-[2-phosphonoalkyleneyl)-phenyl]-2-aminoalkanoic acids having general formula:

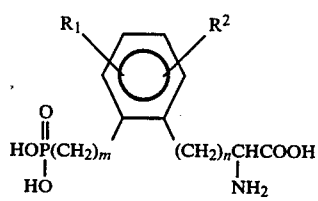

Wherein $R_1$ and $R_2$ are the same or different and are selected from the group consisting of hydrogen, lower alkyl, halogen, —CH=CH—CH=CH—, amino, nitro, trifluoromethyl or cyano; n and m=0, 1, 2, or 3; and the pharmaceutically acceptable salts and derivatives thereof.

Examples of specific preferred compounds of general formula are selected from the group consisting of: 4-[2-phosphonomethylphenyl]-2-aminobutanoic acid, ethyl 3-[2-(2-diethylphosphonoethyl)phenyl]-2-acetamido-2-carboethoxypropanoate, 3-[2-(2-phosphonomethyl)-phenyl]-2-aminopropanoic acid, ethyl 3-[2-(3-bromopropyl)phenyl]-2-acetamido-3-carboethoxypropanoate, ethyl 3-[2-(3-diethylphosphonopropyl)phenyl]-2-acetamido-2-carboethoxypropanoate, ethyl 3-[2-(3-phosphonopropyl)-phenyl]-2-aminopropanoic acid, ethyl 5-[2-(diethylphosphonomethyl)-phenyl]-2-acetamido-2-carboethoxypentanoate, and 5-[2-phosphonomethylphenyl]-2-aminopentanoic acid.

14 Claims, No Drawings

ANTAGONISTS OF SPECIFIC EXCITATORY AMINO ACID NEUROTRANSMITTER RECEPTORS

BACKGROUND OF THE INVENTION

1. Field of the Invention

The present invention pertains to novel, potent anticonvulsants, antiepileptics, analgesics and cognition enhancers achieving their action through the antagonism of specific excitatory amino acid (EAA) neurotransmitter receptors. In particular, the invention is directed to ω-[2-(phosphonoalkylenyl)phenyl]-2-aminoalkanoic acids, their pharmaceutically acceptable salts and derivatives, and to the methods of synthesizing the same.

2. Description of the Prior Art

While L-glutamate and L-aspartate were initially thought merely to participate in brain metabolism, sufficient molecular pharmacological, biochemical and electrophysiological evidence now exists to suggest that these amino acids are neuroexcitatory transmitters [D. R. Curtis, A. W. Duggar, D. Felix, G. A. R. Johnston, A. K. Tebecis and J. C. Watkins. Brain Res. 41:283-301 (1972)].

For many years following the initial characterization of the neuro-excitotoxic actions of amino acis, it was tacitly assumed that all compounds of this type (agonists and antagonists) acted upon the same receptor. The discovery of relatively selective antagonists of different actions of EAA or of actions of different EAA compounds, has changed this perception, and it is now accepted that multiple recognition sites for EAA are present in the vertebrate central nervous system [J. C. Watkins and R. H. Evans. Ann. Rev. Pharmacol. Toxicol. 21:165-204 (1981)]. Defined by prototypical agonists or antagonists, these include:

1. receptors activated by L-Glutamate (Glu) and the conformationally restricted Glu analog, quisqualic acid (Quis), and antagonized selectively by glutamic acid diethylester, 2. receptors responsive to the synthetic analogue of L-aspartate (Asp), N-methyl-D-aspartate (NMDA), the isoxazole neurotoxin, ibotenic acid (Ibo), the pyridinedicarboxylic acid neurotoxin, quinolinic acid (Quin) and, probably, to Asp itself. These receptors are antagonized by D(−)-2-amino-5-phosphonopentanoic acid (AP5), D(−)-2-amino-7-phosphonoheptanoic acid (AP7), and the divalent cation, Mg++, 3. receptors activated by the pyrrolidine neuroexcitotoxin, kainic acid (KA), for which no specific antagonists have yet been identified and, 4. receptors antagonized by L(+)-2-amino-4-phosphonobutyric acid (LAP4). Originally identified as an EAA antagonist by electrophysiological means, LAP4 inhibits the response at the lateral perforant pathway synapses of the hippocampus to an unidentified endogenous excitatory substance. The possibility that Glu is this neurotransmitter is minimal and recent evidence suggests that the N-blocked dipeptide, N-acetylaspartyl-L-glutamate may function in this capacity [J. M. H. ff-French-mullen, K. J. Koller, R. Zaczek, Li Hori, J. T. Coyle and D. O. Carpenter. Proc. Nat. Acad. Sci. USA 82, 3897-4001 (1985)].

EAA's, possibly acting through one or more of these receptors, have been implicated in the etiology of various pathological conditions affecting the CNS. Thus, KA [K. Biziere, J. T. Slevin, R. Zaczek, J. C. Collins and J. T. Coyle. In: *Advances in Pharmacology and Therapeutics* (H. Yoshida, Y. Hagihara and S. Ebashi, eds) Pergamon, New York. pp. 271-276 (1982)], NMDA [R. Zaczek, J. Collins and J. T. Coyle. Neurosci. Letts 24:181-186 (1981)] and the endogenous excitatory amino acid Quin [R. Schwarcz, W. O. Whetsell and R. M. Mango. Science 219:316-318 (1983)] have been used to produce in animal models a syndrome analogous to human epilepsy and other convulsive disorders, and the anatomical and neurochemical lesions and deficiencies produced by such chemicals in animals with these compounds are similar to the characteristics seen postmortem in the brains of patient's dying of Huntington's disease [J. Coyle, and R. Schwarcz. Nature 263:244-246 (1976)] and epilepsy. Kainate administration can produce a limbic structure lesion that mimicks Ammon's Horn Sclerosis, an abnormality frequently found in temporal lobe epilepsy. Research on this model of temporal lobe epilepsy has suggested that endogenous EAA's may play a role in this disorder, that is particularly resistant to existing antiepileptics [J. V. Nadler, B. W. Perry, C. W. Cotman. Nature 271:676-677 (1978)]. In addition to Huntington's disease and epilepsy, it has been suggested that EAA's may contribute to Alzheimer's disease [A. C. Foster, J. F. Collins and R. Schwarcz. Neuropharmac. 22:1331-1341 (1983)], E. Roberts. In: *Strategies for the development of an Effective Treatment for Senile Dementia* (E. Crook and L. Gershon, eds.) Mark Power Assoc., New Camarin, Conn. pp. 247-230 (1981)], the neuronal death following stroke and other factors leading to cerebral ischemia, [R. P Simon, J. H. Swan, T. Griffiths and B. S. Meldrum, Science, 226, 850-852, (1984); S. Rothman. J. Neuroscience 4:1884-1891 (1984)] and hereditary olivopontocerebellar atrophy [J. T. Coyle, TINS 5:287-288 (1982)].

Because of the conceptual link between EAA activity at specific brain receptors in vitro and in vivo, excitotoxic lesions caused by EAA in animals, and the pathogeneis of the above neurodegenerative diseases, it is logical to explore pharmacologic means to antagonize endogenous excitatory and excitotoxic neurotransmitters. The development of antagonists of exogenous excitotoxins such as KA is also logical, since there is presumably and yet undiscovered specific endogenous substance that acts at brain KA receptors. The advent of potent and selective antagonists of EAA's exemplified by α-amino-ω-phosphonoalkylenylcarboxylic acids (the most potent and selective being D(−)-2-amino-7-phosphonoheptanoic acid, D(−)AP7 has provided a point of departure for the pharmacologic intervention of EAA action at their receptors.

Besides interfering with the neurotoxic and convulsive actions of NMDA, the exogenous excitotoxin, IBO, and the endogenous excitotoxin Quin (but not KA) [A. C. Foster and G. E. Fagg. Brain Res. Rev. 7:103-184 (1984); A. C. Foster, J. F. Collins and R. Schwarcz. Neuropharmac. 22:1331-1341 (1983); R. Schwarcz, J. F. Collins and D. A. Parks, Neurosci. Letts 33:85-90 (1982)], AP7 (i.c.v. and i.v.) protects against audiogenically-induced seizures in genetically susceptible mice [M. J. Croucher, J. F. Collins and B. S. Meldrum. Science 216:899-901 (1982)]. I.v. AP7 suppresses photically-induced myoclonus in the baboon [B. S. Meldrum. M. J. Croucher, G. Badman and J. F. Collins, Neurosi. Letts 39:101-104 (1983)], increases threshold current for electroshock induced seizures of mice and prevents chemically induced seizures in rodents [S. J. Czuczwar and G. Meldrum. Eur. J. Pharmac. 83:335–338 (1982)]. Very recently, AP7 (intrahippocampally) has been reported to markedly reduce or eliminate ischemic brain damage in the rodent carotid artery occlusion model of stroke [R. P. Simon, J. H. Swan, T. Griffiths and B. S. Meldrum. Science 226:850–852 (1984)], and another, less potent, EAA antagonist δ-D-glutamyl glycine, has been shown to protect cultured at hippocampal neurones from degeneration under conditions of oxygen depletion while blocking the toxicity of exogenously applied Glu and Asp [S. Rothman. J. Neuroscience 4:1884–1891 (1984)]. Recently, kainate and quisqualate receptor antagonists have also been shown to posses anticonvulsant activity [M. J. Croucher, B. S. Meldrum, A. W. Jones and J. C. Watkins. Brain Res. 377:111–114 (1984)]. Finally, and significantly, several lines of circumstantial evidence link excitatory amino acids, especially glutamate, with the onset of age-associated neurodegenerative diseases, including Alzheimer's disease [J. T. Greenamyre, J. B. Penney, A. B. Young, C. D'Amato, S. P. Hicks, I. Schoulson, Science 227:1496–1498 (1985)], and with tardive dyskinesia [J. W. Olney. In: *Excitotoxins* (K. Fuxe, R. Roberts, and R. Schwarcz, eds)].

SUMMARY OF THE INVENTION

The present invention provides a potent, selective excitatory amino acid neutrotransmitter receptor antagonist having the general formula:

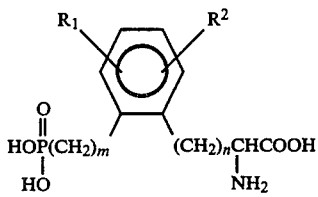

wherein $R_1$ and $R_2$ are the same or different and are selected from the group consisting of hydrogen, lower alkyl, halogen, —CH=CH—CH=CH—, amino, nitro, trifluoromethyl or cyano; n and m=0, 1, 2 or 3; and the pharmaceutically acceptable salts and derivatives thereof.

DETAILED DESCRIPTION OF THE INVENTION

The structure and formulation of the novel compounds of the invention was the result of the extensive research investigation into the antagonism of heterogenic excitatory amino acid neurotransmitter receptors.

Defined by prototypical agonists or antagonists, these include:

1. receptors activated by L-Glutamate (Glu) and the conformationally restricted Glu analog, quisqualic acid (Quis), and antagonized selectively by glutamic acid diethylester, 2. receptors responsive to the synthetic analogues of L-aspartate (Asp), N-methyl-D-aspartate (NMDA), the isoxazole neurotoxin, ibotenic acid (Ibo), the pyridinedicarboxylic acid neurotoxin, quinolinic acid (Quin) and, probably, to Asp itself. These receptors are antagonized by D(−)-2-amino-5-phosphonopentanoic acid (AP5), D(−)-2-amino-7-phosphonoheptanoic acid (AP7), and the divalent cation, Mg++, 3. receptors activated by the pyrrolidine neuroexcitotoxin, kainic acid (KA), for which no specific antagonists have yet been identified and, 4. receptors antagonized by L(+)-2-amino-4-phosphonobutyric acid (LAP4). Originally identified as an EAA antagonist by electrophysiological means, LAP4 inhibits the response at the lateral perforant pathway synapses of the hippocampus to an unidentified endogenous excitatory substance. The possibility that Glu is this neurotransmitter is minimal and recent evidence suggests that the N-blocked dipeptide, N-acetylaspartyl-1-glutamate may function in this capacity [J. M. H. ff-French-mullen, K. J. Koller, R. Zaczek, Li Hori, J. T. Coyle and D. O. Carpenter, Proc. Nat. Acad. Sci. (USA) 82, 3897–4001 (1985)].

The structure of novel compounds provides potent antagonists having greater affinity toward one of the receptors or no affinity to some of them rendering the compound selective. This would therefore permit one to selectively antagonize one EAA receptor in the tissue also containing other EAA receptors. As a result of the greater affinity and selectivity of the present invention fewer side effects are exhibited by the novel compounds.

The high affinity and selectivity of such compounds e.g.: 3-[2-(2-phosphonoethyl)phenyl]-2-aminopropanoic acid or 3-[2-(2-phosphonomethyl)phenyl]-2-aminopropanoic acid, has been demonstrated in receptor binding studies and in mice by their ability to provide protection in pentylenetetrazol (PTZ) induced seizures.

The novel compounds of the invention can be readily prepared by the following synthetics routes:

Route 1

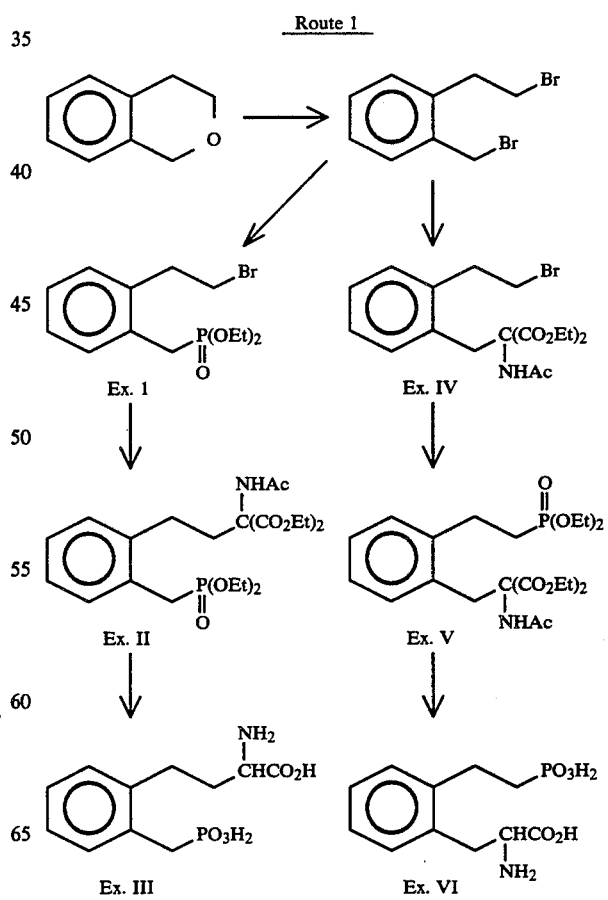

Ex. I

Ex. II

Ex. III

Ex. IV

Ex. V

Ex. VI

In route 1, leading to compounds of examples I and IV, the reaction of isochroman with a solution of hydrobromic and acetic acids in a sealed tube gives the required intermediate o-(2-bromoethyl)benzyl bromide in high yield (Anderson, E. L.; Holliman, F. G. *J. Chem. Soc.*, 1950, 1037). The reaction of this compound with triethylphosphite gives the compound of example I in 70% yield. The compound of example II, ethyl 4-[2-(diethylphosphono-methyl)-phenyl]-2-acetamido-2-carboethoxy-butanoate was prepared by reacting the bromophosphonate described in example I with the sodium salt of diethylacetamidomalonate. Hydrolysis in 6N HCl gives the compound of example III. Alternatively, reacting the intermediate o-(2-bromoethyl)benzyl bromide with the sodium salt of diethyl acetamidomalonate gives the compound of example IV. Reaction of this compound with triethylphosphite gives the compound of example V in 75% yield. Hydrolysis in 6N HCl gives the compound of example VI.

Route 2

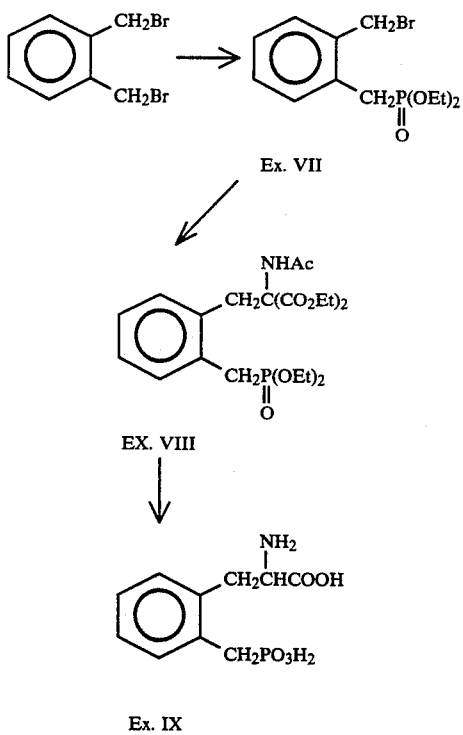

In route 2, the commercially available α,α'-dibromo-o-xylene reacts with triethylphosphite giving the compound of example VII. Reaction of this intermediate with the sodium salt of diethyl acetamidomalonate yields the compound of example VIII. Hydrolysis in 6N HCl gives the compound of example IX.

Route 3

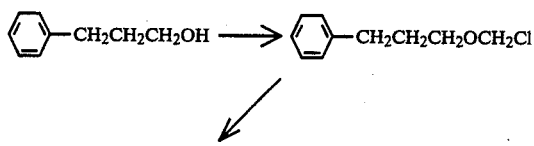

-continued
Route 3

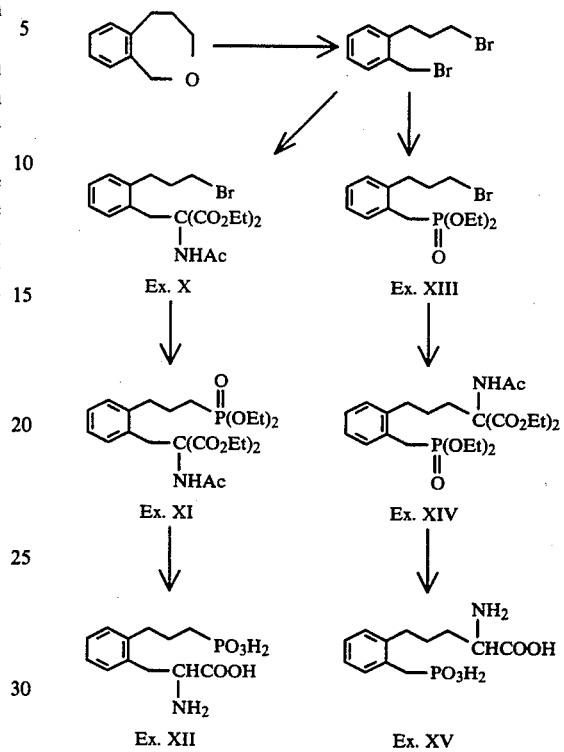

In route 3, it is necessary to synthesize the required intermediate o-(3-bromopropyl)benzyl bromide [Rieche, A.; Gross, H. *Chem. Ber.*, 1962, 91]. Chloromethylation of 3-phenylpropanol gives chloromethyl 3-phenylpropyl ether in high yield. Friedel-Crafts cyclization with $AlCl_3$ in $CS_2$ gives 2-benzoxepine. Reaction of this compound with a solution of hydrobromic acid-acetic acid in a sealed tube yields the required common intermediate o-(3-bromopropyl)benzyl bromide. Reaction of this compound with the sodium salt of diethyl acetamidomalonate yields the compound of example X. Reaction of this compound with triethylphosphite gives the phosphonomalonate compound of example XI. Hydrolysis in 6N HCl gives the compound of example XII. Alternatively, reacting the intermediate o-(3-bromopropyl)benzyl bromide with triethylphosphite gives the compound of example XIII. Reacting this compound with the sodium salt of diethyl acetamidomalonate gives the compound of example XIV. Hydrolysis in 6N HCl gives the compound of example XV.

The preparation of compounds for administration in pharmaceutical preparations may be in a variety of well known methods known to those skilled in the art of pharmacy. More specifically the novel compounds may be formulated as an acid salt, i.e., HCl salt, sulfate, phosphate, nitrate, methanesulfonate, tartrate or a base salt and other pharmaceutically acceptable salts and compositions.

In parenteral administration of the novel compounds and compositions of the invention the compounds may be presented in aqueous injection solutions which may contain antioxidants, buffers, bacteriostats, etc. Extemporaneous injection solutions may be prepared from sterile pills, granules or tablets which may contain diluents, dispersing and surface active agents, binders and lubricants.

In the case of oral administration, fine powders or granules of the compound may be formulated with diluents and dispersing and surface active agents, and may be prepared in a draft in water or in a syrup, in capsules or cachets in the dry state or in a non-aqueous suspension, when a suspending agent may be included. The compounds may also be administered in tablet form along with optional binders and lubricants, or in a suspension in water or a syrup or an oil or in a water/oil emulsion and may include flavoring, preserving, suspending, thickening and emulsifying agents. The granules or tablets for oral administration may be coated and other pharmaceutically acceptable agents and formulations may be utilized as known to those skilled in the art.

The following examples are illustrative of compounds of the invention but are not to be construed as limiting the invention thereto.

EXAMPLES

PREPARATION EXAMPLES

EXAMPLE I

Diethyl 2-(2-Bromoethyl)benzylphosphonate

In a round bottom flask equipped for distillation, 15.0 g (54 mmol) of 2-(2-bromoethyl)benzyl bromide and 9.0 g (54 mmol) of triethylphosphite were heated on an oil bath with stirring at 90°–100° C. When ethyl bromide ceased distilling off (1 h) the remaining volatile by-products and triethylphosphite were removed from the mixture by distillation under vacuum. The viscous oil which remained was chromatographed on a column of silica gel with hexane-ethyl acetate (1:1) as eluant. The combined fractions were concentrated under reduced pressure to yield 12.5 g (70%) of the product as a yellow oil. IR(neat): 2987, 1249, 1170, 1064, 964, 802 cm$^{-1}$. $^1$H NMR(CDCl$_3$) $\delta$ 1.2 (t, 6H); 3.0–4.35 (m, 10H); 7.2 (s, 4H).

EXAMPLE II

Ethyl 4-[2-(diethylphosphonomethyl)phenyl]-2-acetamido-2-carboethoxybutanoate

To 1.03 g (44.8 mmol) of sodium in 50 mL of dry ethanol was added 9.72 g (44.8 mmol) of solid diethyl acetamidomalonate portionwise. This solution was stirred at reflux under nitrogen for 2 h. After cooling to room temperature the solvent was removed under reduced pressure yielding a tan solid. This solid was dried under vacuum about 2 h. The sodium salt of diethyl acetamidomalonate was then suspended in 50 mL of dry toluene and 15.0 g (44.8 mmol) of diethyl 2-(2-bromoethyl)benzylphosphonate in 25 mL of toluene was added dropwise. This solution was stirred at reflux under nitrogen for 36 h. After cooling the solution to room temperature the solid precipitate was removed by filtration and washed with 20 mL of toluene. The combined toluene solutions were concentrated under reduced pressure to yield a viscous oil. This oil was chromatographed on a column of silica gel with ethyl acetate as eluant. The combined fractions were concentrated under pressure to give 7.2 g (34%) of the product as a clear viscous oil. IR(neat): 1745, 1676 (C=O) cm$^{-1}$. $^1$H NMR(CDCl$_3$) $\delta$ 1.0–6 (m, 12H); 1.8–3.2 (complex m, 9H); 3.7–4.6 (m, 8H); 6.8–7.4 (m, 5). Anal. Calcd. for C$_{22}$H$_{34}$NO$_8$P0.5H$_2$O: C, 54.99; H, 7.34; N, 2.92. Found: C, 54.75; H, 7.37; N, 2.97.

EXAMPLE III

4-[2-Phosphonomethylphenyl]-2-aminobutanoic acid

A solution of 2.5 g (5.3 mmol) of ethyl 4-[2-(diethylphosphonomethyl)-phenyl]-2-acetamido-2-carboethoxybutanoate in 50 mL of 6N HCl was stirred at vigorous reflux for 12 h. After cooling to room temperature the reaction mixture was concentrated at reduced pressure yielding an oil. This oil was washed with three 50 mL portions of water then dissolved in 95% ethanol and a slight excess of propylene oxide added. The precipitated acid was collected by filtration and recrystallized from dilute ethanol yielding 1.26 g (77%) of the product as a white solid: mp 247°–249° C. IR(KBr): 1725, 1620 cm$^{-1}$; $^1$H NMR (D$_2$O) $\delta$ 2.0–3.4 (6H unresolved), 3.9–4.3 (m, 1H), 7.4 (s, 4H); Anal. Calcd. for C$_{11}$H$_{16}$NO$_5$P0.5H$_2$O: Calcd: C, 46.62; H, 6.05; N, 4.94. Found: C, 46.73; H, 6.04; N, 4.79.

EXAMPLE IV

Ethyl 3-[2-(2-bromoethyl)phenyl]-2-acetamido-2-carboethoxypropanoate

To a solution of 0.41 g (18 mmol) Na in 100 mL of dry ethanol was added portionwise 3.9 g (18 mmol) of solid diethylacetamidomalonate. This mixture was stirred at reflux under nitrogen for 2 h then cooled to 0°–10° C. Then, 5.0 g (18 mmol) of 2-(2-bromoethyl)benzyl bromide was rapidly added in one portion. The reaction was stirred for 2 h at 0°–10° C. then 24 h at room temperature. The precipitated inorganic salt was removed by filtration and discarded. The solvent was removed under reduced pressure yielding a golden oil. This oil was chromatographed on a reverse phase column (C-18) with methanol-water (1:1) as eluant. The combined fractions were concentrated under reduced pressure to yield 5.6 g (75%) of the product as a white solid, mp 86.0°–86.5° C. IR(nujol): 1785, 1637 cm$^{-1}$ (C=O). $^1$H NMR(CDCl$_3$) $\delta$ 1.2 (t, 6H); 1.9 (s, 3H); 2.8–3.5 (m, 4H), 3.6 (5, 2H); 4.2 (q, 4H); 6.8 (s. 1H); 7.2 (m, 4H). Anal. Calcd. for C$_{18}$H$_{24}$NO$_5$Br: C, 52.18; H, 5.84; N, 3.38. Found: C, 52.26; H, 5.86; N, 3.34.

EXAMPLE V

Ethyl 3-[2-(2-diethylphosphonoethyl)phenyl]-2-acetamido-2-carboethoxy-propanoate A solution of 5 g (1.2 mmol) of ethyl 3-[2-(2-bromoethyl)phenyl]-2-acetamido-2-carboethoxypropanoate in 10 mL of P(OEt)$_3$ was stirred at reflux for 4 h. The excess P(OEt)$_3$ and the volatile by-products were removed from the mixture by distillation under vacuum. The remaining viscous oil was initially purified by column chromatography (C-18, MeOH:H$_2$O; 4:1), then by preparative HPLC (C-18, MeOH:H$_2$O, 7:3) giving 0.48 g (86%) of the product as a clear viscous oil. IR(Nujol) 1745.9, 1676.5 cm$^{-1}$ (C=O); $^1$H NMR(CDCl$_3$) $\delta$ 1.1–1.5 (m, 12H); 1.8–3.1 (complex, m, 7H); 3.7 (s, 2H); 3.8–4.4 (m, 8H); 6.6 (s, 1H), 7.0–7.3 (m, 4H) Anal. Calcd. for C$_{22}$H$_{34}$NO$_8$P: C, 56.04; H, 7.27; N, 2.97. Found: C, 55.91; H, 7.31, N, 2.84.

EXAMPLE VI

3-[2-(2-Phosphonoethyl)phenyl]-2-aminopropanoic acid

A solution of 7.9 g (16.8 mmol) of ethyl 3-[2-(2-diethylphosponoethyl)-phenyl]-2-acetamido-2-carboethoxypropanoate in 40 mL of 6N HCl was stirred at vigorous reflux for 14 h. After cooling to room temperature the reaction mixture was concentrated at reduced pressure yielding an oil. This oil was washed with four 25 mL portions of water then dissolved in 20 mL 95% ethanol and propylene oxide added dropwise. The precipitated crude acid was collected by filtration. Recrystallization from dilute ethanol yielded 4.1 g (90%) as a white solid, mp 241°–243° C. IR(Nujol): 1712.5 cm$^{-1}$ (C=O). $^1$H NMR(D$_2$O) δ 1.5–2.2 (m, 2H); 2.6–3.3 (m, 4H); 3.9–4.2 (t, 1H); 7.2 (m, 4H). Anal. Calcd. for C$_{11}$H$_{16}$NO$_5$P: C, 48.35; H, 5.90; N, 5.13. Found: C, 48.69; H, 6.16; N, 4.95.

EXAMPLE VII

Diethyl 2-(bromomethyl)benzylphosphonate

In a round bottom flask equipped for distillation, 20.0 g (75.8 mmol) of α,α$_1$-dibromo-o-xylene and 12.6 g (75.8 mmol) of triethylphosphite were heated with stirring at 70°–75° C. When ethyl bromide ceased distilling off (about 2–3 h), the remaining volatile by-product and triethylphosphite were removed from the mixture by distillation under vacuum. The remaining oil was chromatographed on a column of silica gel with ethyl acetate as eluant. The fractions were combined and concentrated under reduced pressure to yield a yellow oil. IR(neat): 1249; 1164.8; 1038.8; 966.8; 794.5 cm$^{-1}$. $^1$H NMR (CDCl$_3$) δ 1.0–1.4 (m, 6H); 3.1 (s, 1H); 3.5 (s, 1H); 3.6–4.2 (m, 4H); 4.6 (s, 1H); 7.2 (s, 4H).

Anal. Calculated for C$_{12}$H$_{18}$PO$_3$Br: C.

EXAMPLE VIII

Ethyl 3-[2-(diethylphosphonomethyl)phenyl]-2-acetamido-2-carboethoxy-propanoate To a solution of 0.43 g (18.8 mmol) Na in 50 mL of dry ethanol was added 4.09 g (18.8 mmol) of solid diethyl acetamidomalonate portionwise. This mixture was stirred at reflux under nitrogen for 2 h, then cooled to room temperature. Then, 6.05 g (18.8 mmol) of 2-(diethylphosphonomethyl)benzyl bromide in 40 mL of ethanol was added dropwise and the mixture stirred for 24 h. The salt which precipitated was removed by filtration and the solvent concentrated at reduced pressure to yield a viscous oil. This oil was chromatographed on a column of silica gel with ethyl acetate as eluant. The combined fractions were concentrated under reduced pressure to yield 6.67 g (79%) of the product as a clear oil. IR(neat): 1745.9, 1676.5, 1501.6, 1375.6, 1247.1, 1649.1, 969.4 cm$^{-1}$. $^1$H NMR (CDCl$_3$) δ 1.0–1.4 (m, 12H); 2.0 (s, 3H); 2.9 (s, 1H); 3.3 (s, 1H); 3.8–4.4 (m, 10H); 5.8–7.4 (m, 5H). Anal. Calcd. for C$_{21}$H$_{32}$NPO$_8$0.5H$_2$O: C, 54.06; H, 6.92; N, 3.00. Found: C, 53.73; H, 7.11; N, 3.27.

EXAMPLE IX

3-[2-Phosphonomethylphenyl]-2-aminopropanoic acid 532

A solution of 4.5 g (9.8 mmol) of ethyl 3-[2-(diethylphosphonomethyl-phenyl]-2-acetamido-2-carboethoxypropanoate in 50 mL of 6N HCl was stirred at vigorous reflux for 12 hours. After cooling to room temperature the reaction mixture was concentrated at reduced pressure yielding an oil. This oil was washed with three 50 mL portions of water then dissolved in 95% ethanol and an excess of propylene oxide added. The precipitated acid was collected by filtration and recrystallized from dilute ethanol yielding 1.6 g (63%) of the product as a white solid: mp 259°–261° C.; IR(nujol): 1722; 1625; 1128; 1049 cm$^{-1}$. $^1$H NMR(D$_2$O) δ 2.8–3.7 (unresolved, 4H), 4.2 (m, 1H), 77.3 (s, 4H); Anal. Calcd. for C$_{10}$H$_{14}$NO$_5$P, 0.25H$_2$O: C, 45.55; H, 5.54; N, 5.32. Found: C, 45.57, H, 5.55; N, 5.38.

EXAMPLE X

Ethyl 3-[2-(3-bromopropyl)phenyl]-2-acetamido-2-carboethoxypropanoate

To a stirred solution of 0.61 g (27 mmol) Na in 40 mL of dry ethanol was added portionwise 5.86 g (27 mmol) of solid diethyl acetamidomalonate. This mixture was stirred at reflux under nitrogen for 2 h, then cooled to 0°–10° C. on an ice bath. Then, 8.0 g (27 mmol) of 2-(3-bromopropyl)benzyl bromide in 40 mL of dry ethanol was rapidly added. The reaction mixture was stirred for 2 h at 0°–10° C., then 24 h at room temperature. The precipitated inorganic salt was removed by filtration, and was washed with 20 mL of ethanol and discarded. The combined solvents were removed under reduced pressure yielding an orange colored oil. This oil was chromatographed on a column of silica gel with hexane-ethyl acetate (3:1) as eluant. The combined fractions were concentrated under reduced pressure to yield an oil which solidified upon standing, yield 9.5 g (82%), mp 73°–74.5° C. IR(nujol): 1745, 1648 cm$^{-1}$ (C=O). $^1$H NMR(D$_2$O) δ 1.3 (t, 6H); 1.9–2.4 (m, 5H); 2.7 (t, 2H); 3.4 (t, 2H); 3.75 (5, 2); 4.3 (q, 4); 6.6 (s, 1H); 7.0–7.3 (m, 4H). Anal Calcd. for C$_{19}$H$_{26}$NO$_3$Br: C, 53.28; H, 6.12; N, 3.27; Br, 18.66. Found: C, 53.33; H, 6.13; N, 3.23; Br, 18.67.

EXAMPLE XI

Ethyl 3-[2-(3-diethylphosphonopropyl)phenyl]-2-acetamido-2-carboethoxy-propanoate A solution of 7.5 g (17.5 mmol) of ethyl 3-[2-(3-bromopropyl)phenyl]-2-acetamido-2-carboethoxy-propanoate in 20 mL of freshly distilled triethylphosphite was stirred at reflux for 6 h. The excess P(OEt)$_3$ and the volatile by-products were removed from the mixture by distillation under vacuum. The remaining viscous oil was chromatographed on a column of silica gel with ethyl acetate as eluant. The combined fractions were concentrated under reduced pressure to yield 4.2 g (49%) of the product as a viscous yellow oil. IR(neat): 1746, 1680 cm$^{-1}$ (C=O). $^1$H NMR(CDCl$_3$) δ 1.1–2.1 (complex m, 19H); 2.4–2.7 (t, 2H); 3.6 (5, 2H); 3.8–4.3 (m, 8H); 6.55 (s, 1H); 6.9–7.2 (m, 4H).

EXAMPLE XII

3-[2-(3-Phosphonopropyl)phenyl]-2-aminopropanoic acid

A solution of 3.0 g (6.9 mmol) of ethyl 3-[2-(diethylphosphonopropyl)phenyl]-2-acetamido-2-carboethoxy-propanoate in 25 mL of 6N HCl was stirred at vigorous reflux 12 h. After cooling to room temperature the reaction mixture was concentrated at reduced pressure yielding an oil. The oil was washed with three 25 mL portions of water then dissolved in 25 mL 95% ethanol and propylene oxide added dropwise. The precipitated acid was collected by filtration. Recrystallization from dilute ethanol yield 0.76 g (38%) as a white solid mp>95° C. (dec.). IR(nujol): 1717.6 cm$^{-1}$ (C=O). $^1$H NMR(D$_2$O) δ 1.1–2.0 (complex m, 4H); 2.6–3.1 (m, 4H); 3.35–3.65 (m, 1H); 7.3 (m, 4H). Anal. Calcd. for: C$_{12}$H$_{18}$NO$_5$P.H$_2$O: C, 47.21; H, 6.60; N, 4.58. Found: C, 47.47; H, 6.72; N, 4.53.

EXAMPLE XIII

Diethyl 2-(3-bromopropyl)benzylphosphonate

In a round bottom flask equipped for distillation, 11.36 g (38.9 mmol) of 2-(3-bromopropyl)benzyl bromide and 6.46 (38.9 mmol) of freshly distilled triethylphosphite were heated with stirring at 100°–110° C. on an oil bath. When ethyl bromide ceased distilling off (about 2 h) the remaining volatile by-products and the triethylphosphite were removed from the mixture by distillation under vacuum. The remaining oil was chromatographed on a column of silica gel with hexame-ethyl acetate (1:1) as eluant. The combined fractions were concentrated under reduced pressure to yield 11.2 g (83%) of the product as a clear oil. IR(neat): 2985, 1496, 1450, 1391, 1252, 1162, 104, 967, 843, 802, 758 cm$^{-1}$. $^1$H NMR(CDCl$_3$) δ 1.2 (t, 6); 1.8–2.3 (m, 2H); 2.7–3.55 (m, 4H); 3.8–4.2 (m, 2H); 7.1–7.4 (m, 4H).

EXAMPLE XIV

Ethyl 5-[2-(diethylphosphonomethyl)phenyl]-2-acetamido-2-carboethoxypentanoate

To 0.48 g (21 mmol) of sodium in 50 mL of dry ethanol was added 4.56 g (21 mmol) of solid diethyl acetamidomalonate portionwise. This solution was stirred at reflux under nitrogen for 2 h. After cooling to room temperature the solvent was removed under reduced pressure yielding a tan solid. This solid was dried under vacuum about 2 h. The sodium salt of diethyl acetamidomalonate was then suspended in 50 mL of dry toluene and 9.0 g (21 mmol) of diethyl 2-(3-bromopropyl)benzylphosphonate in 25 mL of dry toluene was added dropwise. This solution was stirred at reflux under nitrogen for 20 h. After cooling to room temperature the solid which precipitated was removed by filtration and washed with toluene. The combined toluene solutions were concentrated under reduced pressure to yield a dark oil. This oil was chromatographed on a column of silica gel with ethyl acetate as eluant. The combined fractions were concentrated under reduced pressure yielding 4.2 g (42%) of the product as a yellow viscous oil which solidified upon standing, mp 76°–79° C. IR(neat) 1745.9, 1680 cm$^{-1}$ (C=O). $^1$H NMR(CDCl$_3$) δ 1.0–1.4 (m, 12H); 2.0 (s, 3H); 2.2–3.3 (m, 6H); 3.7–4.4 (m, 8H); 6.8 (5, 1H); 7.0–7.3 (m, 4H). Anal. Calcd. for C$_{23}$H$_{36}$NO$_8$P: C, 56.90; H, 7.48; N, 2.89. Found: C, 56.27; H, 7.51; N, 2.86.

EXAMPLE XV

5-[2-Phosphonomethylphenyl]-2-aminopentanoic acid

A solution of 3.8 g (7.8 mmol) of Ethyl 5-[2-diethylphosphonomethyl)phenyl]-2-acetamido-2-carboethoxypentanoate in 25 mL of 6N HCl was stirred at vigorous reflux for 12 h. After cooling to room temperature the reaction mixture was concentrated at reduced pressure yielding an oil. This oil was washed with three 25 mL portions of water then dissolved in 25 mL of 95% ethanol and propylene oxide was added dropwise. The precipitated crude acid was collected by filtration. Recrystallization from dilute ethanol yielded 1.7 g (76%) of the product as a white solid, mp>152° C. (dec.). IR(nujol): 1717.6 cm$^{-1}$ (C=O). $^1$H NMR(D$_2$O) δ 1.6–1.9 (broad, 4H); 2.8–3.3 (m, 4H); 3.45 (m, 1H); 7.3.7.7 (m, 4H). Anal. Calcd. for C$_{12}$H$_{18}$NO$_5$P. 0.5H$_2$O: C, 48.65; H, 6.46; N, 4.73. Found: C, 48.56, H, 6.46; N, 4.72.

EXAMPLE XVI

In vitro Receptor Binding Assays

The potency of the compounds described in examples III, V, VI, IX, XII and IV to inhibit the specific binding of various excitatory amino acid ligands to rat brain membranes was examined using standard in vitro ligand binding techniques. Specifically, compounds were evaluated for potency to inhibit the specific binding of [$^3$H]kainic acid, [$^3$H]KA, RS-α-amino-3-hydroxy-5-methyl-4-isoxazolepropionic acid [$^3$H]AMPA, [$^3$H]DL(±)2-amino-7 phosphono heptanoic acid [$^3$H]AP7.

The methods were as follows: rat forebrain membranes were prepared as described by Enna and Synder (Mol. Pharmacol, 13, 422–453, 1977) and the final pellet was washed three additional times by centrifugation (45,000 g; 10 min; 4° C.) with intermittent resuspensions (20 vol; w/v) in fresh buffer appropriate to the assay. For the [$^3$H]AP4 assay, tissue was used immediately. For all other procedures, tissue was stored frozen (−40° C.) until use. All assays were performed using triplicate incubations. Radioactivity was determined using conventional liquid scintillation counting after solubilizing the pellet in 1 mL Protosol (New England Nuclear, Boston, MA) and following the addition of 6 mL of Enconofluor (New England Nuclear, Boston, MA).

Specific [$^3$H]AP4 (specific activity (S.A.)=26.1 Ci/mmol, New England Nuclear, Boston, MA) binding was studied according to the method of Butcher et al. (Brit. J. Pharmacol., 80, 355–364, 1983) using HEPES KOH buffer (0.05 M; pH 7.1). Incubations (2mL) were conducted for 45 min at 37° C. and the reaction was terminated by centrifugation (45,000 g; 10 min; 4° C.). The supernatant was decanted and the pellet washed rapidly and superficially with 2×3.5 ml of ice cold buffer. Final ligand concentration in the assay was 50 nM and L-glutamate (10$^{-3}$M) was used to define non specific binding.

Specific [$^3$H]AMPA (S.A.=25.6 Ci/mmol, New England Nuclear) binding was examined according to the method of Murphy et al., (Soc. Neurosci. Abs., 11, 109, 1985) using Tris HCL buffer (0.05M, pH 6.9; 23° C.) containing 100 mM KSC. Following pretreatment of tissue with Triton-X-100 (0.05%; v/v) for 30 min (37° C.) incubations (2 mL) were conducted for 60 min at 4° C.). The supernatant was decanted and the pellet washed rapidly and superficially with 2×3.5 mL of ice cold buffer. Final ligand concentration in the assay was 16 nM and L-glutamate (10$^{-3}$M) was used to define nonspecific binding.

Specific [$^3$H]AP7 (S.A.=58.4 Ci/mmol, New England Nuclear) binding was examined as described by Ferkany and Coyle (Life Sci., 33, 1295–1305, 1983) using Tris citrate buffer (0.05M; pH 7.5; 23° C.). Following preincubation of the tissue (30 min; 37° C.), incubation (2 ml) were conducted for 90 min at 37° C.

and the reaction was terminated by centrifugation (45,000 g; 10 min; 4° C.). The supernatant was decanted and the pellet washed rapidly and superficially wth 2×3.5 mL of ice cold buffer. Final ligand concentration in the assay was 500 nM and L-glutamate ($10^{-3}$M) was used to define nonspecific binding.

Specific [$^3$H]KA (S.A.=60 Ci/mmol, New England Nuclear) binding was examined according to the methods of London and Coyle (Mol. Pharmacol., 15, 492–505, 1979) using Tris HC; buffer (0.05M; pH 7.4; 23° C.). Incubations 2 mL) were performed for 90 min at 4° C.) and the reaction terminated by centrifugation 45,000 g; 10 min; 4° 1 C.). The supernatant was decanted and the pellet washed rapidly and superfically with 2×3.5 ml of ice cold buffer. Final ligand concentration in the assay was 5 nM and L-glutamate (10-M) was used to define nonspecific binding.

Results are reported in Table 1. When tested at final concentration of 100 uM compounds III, V, VI, IX, XII and IV inhibited less than 20 percent of specifically bound [$^3$H]KA or [$^3$H]AMPA. Similarly, compound IX failed to inhibit the specific binding of [$^3$H]AP4 and [$^3$H]AP7 when tested at 100 uM concentration. Compounds III, VI, XII and XV inhibited the specific binding of [$^3$H]AP4 and [$^3$H]AP7 in a concentration dependent manner with the order of potency in each assay being XV>III>XII≧VI. Whereas compounds III, XII and XV were equipotent to the α-amino-ω-phosphono acid, DL(±)AP7 to inhibit both specific [$^3$H]AP4 and [$^3$H]AP7 binding, compound VI was 3–10 fold less potent in this regard. Further, compound VI effectively discriminated between the two assays and was more potent to inhibit the specific binding of [$^3$H]AP7 than the binding of [$^3$H]AP4.

TABLE I

Potency of Example Compounds to Inhibit Specific [$^3$H] Excitatory Amino Acid Binding to Rat Brain Membranes

| Example | $IC_{50}$(uM) | | | |
|---|---|---|---|---|
| | [$^3$H]AP4 | [$^3$H]AP7 | [$^3$H]Kainate | [$^3$H]AMPA |
| XV | 1.03 | 2.29 | >>100 | >>100 |
| III | 6.8 | 6.1 | >>100 | >>100 |
| XII | 9.5 | N.T. | >>100 | >>100 |
| VI | 16.7 | 52.5 | >>100 | >>100 |
| IX | >>100 | >>100 | >>100 | >>100 |
| V | >>100 | >>100 | >>100 | N.T. |
| AP7 | 5.1 | 6.8 | >>100 | >>100 |

Methods have been described in the text. Values shown are the means of at least three separate determinations performed in triplicate and using eight concentrations of drug. Where values are >>100 uM, this indicates the highest concentration of drug tested and, that less than 20 percent of the specifically bound ligand was displaced.

EXAMPLE XVII

Protection Against Maximal Electroshock Seizures (MES)

The anticonvulsant properties of compounds III, V, VI, IX, XII and XV and, of the reference compound DL(±)P7 against seizures induced by maximal electroshock were evaluated.

For testing, electrodes were clipped to the ears of male CF-1 mice (20–25 g; Charles Rivers), and a current of 0.5 mA was delivered for 0.2 seconds to produce seizures. Anticonvulsant activity was indicated by abolition of the extensor component of the seizure and was defined as hindlimb extension that did not exceed the 90 degree angle with the plane of the body. Data was calculated as the percent of mice not displaying hindlimb extension as described.

Drugs were disolved in a solution of propylene glycol and distilled water (5:95; v/v). For i.c.v. administration, drugs were administered in a final volume of 5 uL, fifteen minutes prior to testing. For i.p. administration, drugs were delivered in a volume of 12.5 ml/kg, thirty minutes prior to testing.

Results are reported in Table 2. As expected, the reference compound AP7 afforded dose-dependent protection against MES-induced seizures with calculated $ED_{50}$'s of 8.4 ug (n=8) and 127 mg/kg (n=16) following i.c.v. and i.p. injection, respectively. When tested at a mole dose equivalent to 1 times or twice the $ED_{50}$ of the reference compound, examples III, V, VI, XII and XV were without effect on MES-induced convulsions by either route of administration. Example IX afforded limited protection against MES-induced seizures with an estimated $ED_{50}$ of 15 ug (i.c.v.) and $ED_{25}$ of 500 mg/kg (i.p). Higher doses of the example IX could not be tested due to the appearance of marked ataxia in some animals.

TABLE II

Potency of Example Compounds to Antagonize Maximal Electroshock of Pentylenetetrazol-Induced Seizures in Male CF-1 Mice

| Example | $ED_{50}$ | | | |
|---|---|---|---|---|
| | MES | | PTZ | |
| | i.c.v. (ug) | i.p. (mg/kg) | i.c.v. (ug) | i.p. (mg/kg) |
| AP7 | 8.3 | 127 | 1.8 | 199 |
| VI | >100 | N.T. | 3.2 | >>350 |
| IX | 16 | 500* | 24 | >>250 |
| V | >>100 | N.T. | >>28 | 350** |
| III | N.T. | >>250 | >>6 | >>500 |
| XII | >>23 | >>155 | >>5 | >>300 |
| XV | >>22 | >>150 | >>5 | >>300 |

Methods have been described in the text. Where $ED_{50}$ values are shown, dose response curves were generated using at least 5 concentrations of the indicated agent with 6-8 animals at each drug concentration. Where $ED_{50}$ is shown as (>>) this indicates the maximum drug dose tested and the fewer than 20 percent of the tested animals were protected.
*highest drug dose tested; $ED_{25}$
**highest drug dose tested; 50 percent of animals protected from seizures; 3 of 7 animals dead prior to end of observation period.

EXAMPLE XVIII

Protection Against Pentylenetetrazol-induced Seizures (PTZ)

The anticonvulsant properties of compounds III, V, VI, IX, XII and XV and, of the reference compound, DL(±)AP7 against seizures induced by pentylenetetrazol (PTZ) were examined.

For testing, PTZ was dissolved in saline (0.9%; w/v) and administered to male CF-1 mice (Charles Rivers; 20–25 g) at a dose of 85 mg/kg fifteen minutes (i.c.v.) or thirty minutes (i.p.) after the administration of the test compound. Mice were observed for ten minutes following the administration of PTZ and seizures were scored as present or absent. Data were expressed as the percent of animals showing seizures activity.

For testing, examples V, VI, XLL, XV and the reference compound were dissolved in propylenegylcol and water (95:5, v/v) whereas examples III and IX were dissolved in 0.2M bicarbonate. Drugs were administered in a volume of 5 uL or 12.5 mL/kg for i.c.v. and i.p. administration, respectively.

Results of testing are shown in Table 2. When administered at drug amounts equal to 1 times or 2 times the $ED_{50}$ of the reference compound to attenuate PTZ-induced seizures, examples III, XII and XV were devoid of activity followed i.c.v. or i.p. administration. Example V, intermediary compound to the synthesis of example VI, provided limited seizure protection (4 of 7 animals) following i.p. injection of 350 mg/kg. Administration of higher doses (500 mg/kg) of example V resulted in mortality in 40 percent of the tested animals and seizure protection was not scored.

Example VI was equipotent to the reference compound to attenuate PTZ-induced convulsions following i.c.v. administration (Table 2). However, following i.p. administration at doses up to 350 mg/kg. example VI failed to significantly protect animals in this seizure model.

Example IX was similarly potent to protect mice from PTZ-induced seizure activity when administered intraventricularly having an ED$_{50}$ 10-fold greater than the reference compound and 6-fold greater than example VI. As was the case for example VI, example IX was essentially devoid of anticonvulsant activity when administered via intraperitoneal injection.

Compounds VI and IX are potent anticonvulsants in the PTZ-induced seizure model following i.c.v. administration and are distinguished from the reference compound by their selectivity to confer protection in this model vis-a-vis MES-induced seizure activity.

What is claimed is:

1. A potent selective excitatory amino acid neurotransmitter receptor antagonist having the general formula:

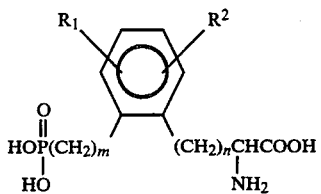

wherein $R_1$ and $R_2$ are the same or different and are selected from the group consisting of hydrogen, lower alkyl, halogen, amino, nitro, triflouromethyl or cyano, or taken together are —CH=CH—CH=3 CH—; n an $m=0, 1, 2,$ or 3; and the pharmaceutically acceptable salts and the 2-acetamido-2-carboethoxy esters thereof.

2. The potent selective excitatory amino acid neurotransmitter receptor antagonist of claim 1 wherein $R_1R_2=$—CH=CH—CH=CH— and $n=1$ and $m=2$ and the 2-acetamido-2-carboethoxy esters thereof.

3. The compound according to claim 1 that is 4-[2-phosphonomethylphenyl]-2-amino-butanoic acid.

4. The compound according to claim 1 that is ethyl 3-[2-(2-diethylphosphonoethyl)-phenyl]-2-acetamido-2-carbethoxypropanoate.

5. The compound according to claim 1 that is 3-[2-(2-phosphonoethyl)-phenyl]-2-aminopropanoic acid.

6. The compound according to claim 1 that is 3-[2-phosphonomethylphenyl]-2-amino-propanoic acid.

7. The compound according to claim 1 that is 3-[2-(3-phosphonopropyl)-phenyl]-2-aminopropanoic acid.

8. The compound according to claim 1 that is 5-[2-phosphonomethylphenyl]-2-amino-pentanoic acid.

9. A pharmaceutical composition for relieving pain which comprises a pain relieving effective amount of one or more compounds of claim 1 with a pharmaceutically acceptable carrier and/or diluent.

10. A process of relieving pain in an animal in need thereof which comprises administering said compound of claim 1 parenterally, nasally, orally, rectally or a combination thereof to said animal in need thereof.

11. A pharmaceutical composition for treatment of convulsions or epilepsy which comprises an effective amount of one or more compounds of claim 1 with a pharmaceutically acceptable carrier and/or diluent.

12. A process for treating convulsions or epilepsy which comprises administering said compound of claims 1 parenterally, orally, nasally, rectally or a combination thereof to said animal in need thereof.

13. A pharmaceutical composition of enhancing cognition which comprises a cognition enhancing amount of one or more compounds of claim 1 with a pharmaceutically acceptable carrier and/or diluent.

14. A process for enhancing cognition which comprises administering said compound of claim 1 parenterally, orally, nasally, rectally or a combination thereof to said animal in need thereof.

* * * * *